United States Patent [19]

Baydar et al.

[11] Patent Number: 5,306,706
[45] Date of Patent: Apr. 26, 1994

[54] PERFUME BASES

[75] Inventors: Ahmet E. Baydar, Cannes; Ghislaine-Henriette Caylus; Christof B. Selden, both of Grasse, all of France

[73] Assignee: Givaudan-Roure Corporation, Clifton, N.J.

[21] Appl. No.: 956,023
[22] PCT Filed: Apr. 11, 1992
[86] PCT No.: PCT/EP92/00823
  § 371 Date: Dec. 7, 1993
  § 102(e) Date: Dec. 7, 1993
[87] PCT Pub. No.: WO92/18097
  PCT Pub. Date: Oct. 29, 1992

[30] Foreign Application Priority Data

Apr. 20, 1991 [EP] European Pat. Off. ......... 91106402.0

[51] Int. Cl.$^5$ ................................................ A61K 7/46
[52] U.S. Cl. ............................................. 512/2; 512/3
[58] Field of Search ................................. 512/1, 2, 3

[56] References Cited

FOREIGN PATENT DOCUMENTS

| 2341927 | 4/1975 | Fed. Rep. of Germany | 512/2 |
| 2351864 | 4/1975 | Fed. Rep. of Germany | 512/2 |
| 2354517 | 5/1975 | Fed. Rep. of Germany | 512/2 |
| 2432484 | 1/1976 | Fed. Rep. of Germany | 512/2 |

OTHER PUBLICATIONS

M. Fontana et al., Riv. Ital. Essenze, Profumi, Piante Off., Aromi, Saponi, Cosmetici, Aerosol (1974), 56, 315-336.
H. Bergerhausen, Cosmetics and Toiletries, 91 (1976) 25-26.
Manufacturing Chemist, Oct. 1989, 22-27.
Inoue et al, Chem. Abst., vol. 93, #88,256s (1980).

*Primary Examiner*—James H. Reamer
*Attorney, Agent, or Firm*—George M. Gould; George W. Johnston

[57] ABSTRACT

Perfume base, containing usnic acid and a perfumery raw material exhibiting an aromatic ring.

6 Claims, No Drawings

PERFUME BASES

Usnic acid, a natural well-known antimicrobial agent, has been demonstrated to be extremely effective against Gram-positive bacteria, fungi, and yeast with Minimum Inhibitory Concentrations as low as 10 ppm for certain species [M. Fontana, G. Proserpio, Riv. Ital. Essenze, Profumi, Piante Off., Aromi, Saponi, Cosmetici, Aerosol (RIPOAM), 1974, 56, 315–336]. The use of free usnic acid in cosmetic formulations is complicated due to its insolubility in all commonly used solvent systems [H. Bergerhausen, Cosmetics and Toiletries 1976, 91, 25–26; Manufacturing Chemist 1989, 22–27]. Soluble derivatives of usnic acid, such as its alkali and ammonium salts, as well as certain esters, have been reported [Handelsgesellschaft Schlosser GmbH, 1975, Ger. Offen. 2354517. Orissa Drebing GmbH, 1975, Ger. Offen. 2351927. Orissa Drebing GmbH, 1975, Ger. Offen. 2351864. Orissa Drebing GmbH, 1976, Ger. Offen. 2432484.]. The major drawbacks of these derivatives are their insufficient stability properties, such as decolorization, pH-sensitivity, and reduction of antimicrobial activity.

Usnic acid [$C_{18}H_{16}O_7$, 2,6-Diacetyl-7,9-dihydroxy-8,9b-dimethyl-1,3(2H,9bH)-dibenzofurandione] exhibits the following characteristics:

MW 344.32; mp 201°–203° C., $[\alpha]_D + 488°$ (c 0.4,$CHCl_3$); mp 204° C.,$[\alpha]_D + 509.4°$ (c0.697,$CHCl_3$);

Solubility at 25° C. (g/100 ml): water<0.01, acetone 0.77, ethyl acetate 0.88, ethanol 0.02, chloroform 4.6, pyridine 2.12, benzene 0.94, dioxane 0.99, isopropyl alcohol 0.28, propylene glycol<0.01, dipropylene glycol 0.01, diethyl phthalate 0.45.

Certain perfumery raw materials now have been found to solubilize usnic acid—and leading to stable solutions. This finding allows the direct use of usnic acid, this natural antimicrobial agent isolated from alpine lichen, in numerous types of perfumes, cosmetic and toiletry formulations, without the usually required derivatization to improve its solubility.

The natural and synthetic perfumery raw materials are all characterized by exhibiting an aromatic ring. In the foreground of the interest are such standard perfumery materials as:

benzyl salicylate (1), benzyl benzoate (2), anisic aldehyde (3), isoeugenol methylether (4), cinnamyl acetate (5), and eugenol (6).

These perfumery raw materials exhibiting the desired solubilizing property are thus not only odorants, but also fixatives, blenders and modifiers.

The amount of any of (1) to (6) in the perfume bases is not too critical. Convenient amounts are:

about 20 to about 90% of any of (1) to (6). Mixtures of any one of (1) to (6) are also possible.

The maximum solubility (g/100 ml) of pure usnic acid in the above pure compounds (1) to (6) at 25° C. is:

benzyl salicylate 3.01, benzyl benzoate 1.93, anisic aldehyde 4.06, isoeugenol methylether 2.69, cinnamyl acetate 1.60, eugenol 2.18, anethol 4.30.

EXAMPLES

Three formulae of perfume compositions containing different concentrations of free usnic acid are listed below:

| Formula 1. | |
|---|---|
| Compound | wt. % |
| Usnic Acid | 0.5 |
| 1 | 20.0 |
| 2 | 18.0 |
| 6 | 2.0 |
| Linalool | 8.0 |
| Benzyl Acetate | 8.0 |
| Hexyl Cinnamic Aldehyde | 13.5 |
| Phenyl Ethyl Alcohol | 2.0 |
| Hydroxycitronellal | 4.0 |
| Ylang Ylang Oil | 2.0 |
| Aldehyde C-14 | 6.0 |
| Aldehyde C-18 | 6.0 |
| Methyl Anthranilate | 4.0 |
| Indolene-50 [8,8-bis-(3H-indol-3-yl)-2,6-dimethyl-2-octanal 50% in castor oil] | 2.0 |
| Methyl Salicylate | 4.0 |
| | 100.00 |

| Formula 2. | |
|---|---|
| Compound | wt. % |
| Usnic Acid | 1.50 |
| 1 | 70.0 |
| 2 | 7.0 |
| 4 | 0.30 |
| Linalool | 1.00 |
| Benzyl Acetate | 7.00 |
| Linalyl Acetate | 0.70 |
| Hexyl Cinnamic Aldehyde | 2.30 |
| Phenyl Ethyl Alcohol | 3.00 |
| Hydroxycitronellal | 5.70 |
| Geraniol Extra | 0.30 |
| Cinnamic Alcohol | 0.15 |
| Aldehyde C-14 (10% in DEP) | 0.15 |
| Aldehyde C-16 (10% in DEP) | 0.15 |
| Aldehyde C-18 (10% in DEP) | 0.30 |
| Argeol [hydroxycitronellal-methyl anthranilate Schiff base] | 0.15 |
| α-Ionone | 0.30 |
| | 100.00 |

| Formula 3. | |
|---|---|
| Compound | wt. % |
| Usnic Acid | 2.00 |
| 1 | 85.0 |
| 2 | 0.80 |
| 6 | 0.20 |
| Linalool | 0.80 |
| Phenyl Ethyl Alcohol | 6.70 |
| Geraniol Extra | 0.90 |
| Citronellol Extra | 0.90 |
| Geranyl Acetate | 0.90 |
| Phenyl Aethyl Acetate | 0.80 |
| Diphenyl Oxide (10% in DEP) | 0.01 |
| Aldehyde C-9 (10% in DEP) | 0.02 |
| Aldehyde C-18 (10% in DEP) | 0.02 |
| Methyl Ionantheme-100 [α-methyl ionone] (10% in DEP) | 0.02 |
| Iso Menthone (10% in DEP) | 0.08 |
| Rose Oxide (10% in DEP) | 0.04 |
| Methyl Octine Carbonate (10% in DEP) | 0.01 |
| Phenyl Aethyl Phenyl Acetate | 0.80 |
| | 100.00 |

Perfume compositions containing free usnic acid can thus be readily incorporated in the usual manner and using the well-known techniques into perfumed consumer products, e.g. into a wide variety of cosmetic and toiletry formulations, such as deodorants, antiperspirants, shower gels, soaps, sanitary pads, skin creams, lotions, tooth paste, mouth wash, etc. Such tooth paste may contain the usual ingredients such as abrasives, surfactants, humectants, binders, therapeutic ingredient(s), if necessary, anti tartar ingredients, preservatives, whiteners, etc.

Two example formulations of applications in a deodorant stick and a deodorant non-aerosol spray are given below.

| Deodorant Stick: | |
| --- | --- |
| Propylene glycol | 63.00% |
| Sodium stearate | 5.00% |
| Deionized water | 25.00% |
| Hydroxyethylcellulose (Natrosol 250) | 0.20% |
| Isostearamidopropyl PG diethyl ammonium chloride (Lexquat AMG-IS) | 2.00% |
| Lauramide DEA (Standamid LD>) | 4.00% |
| Formula 1 (or 2, or 3) | 0.80% |
| | 100.00% |

| Non-Aerosol Deodorant Spray: | |
| --- | --- |
| Propylene glycol | 3.00% |
| Water | 20.50% |
| Ethanol | 75.00% |
| Formula 1 (or 2, or 3) | 1.50% |
| | 100.00% |

Shower gel:
Conventional shower gels, such as described in
Cosmetic & Toiletries 104 (1989), 84 seq., in particular 86, or in
Cosmetic & Toiletries 99 (1984) 96
may contain for example 0,80 parts and 3,00 parts per weight, respectively, of Fragrance Formula 1 (or 2, or 3)

| Tooth paste: | |
| --- | --- |
| Calcium carbonate | 50.00% |
| Sodium lauryl sulphate | 1.50% |
| Glycerol | 10.00% |
| Sorbitol | 15.00% |

| -continued | |
| --- | --- |
| Tooth paste: | |
| Gum tragacanth | 1.50% |
| Sodium monofluorophosphate | 0.90% |
| Tetrasodium pyrophosphate | 0.25% |
| Zinc citrate trihydrate | 0.50% |
| Saccharin | 0.10% |
| Formaldehyde (40%) | 0.06% |
| anethol based perfume or flavour | 1.00% |
| Water to | 100.00% |

The usnic acid in anethol is conveniently ca. 1.5 to 2.5% per weight.

We claim:

1. Perfume base, comprising usnic acid in combination with a perfumery raw material, which is selected from the group consisting of benzyl salicylate, benzyl benzoate, anisic aldehyde, isoeugenol methylether, cinnamyl acetate, eugenol and anethol, the concentration of usnic acid being from about 0.3% w/w to about 3% w/w.

2. Perfume base according to claim 1, wherein the perfumery raw material is selected from the group consisting of benzyl salicylate, benzyl benzoate, anisic aldehyde, isoeugenol methylether, cinnamyl acetate and eugenol.

3. A method for improving the solubility of usnic acid in a perfume composition which comprises incorporating into said perfume composition a perfumery raw material which is selected from the group consisting of benzyl salicylate, benzyl benzoate, anisic aldehyde, isoeugenol methylether, cinnamyl acetate, eugenol and anethol, and wherein the usnic acid is employed in a concentration from about 0.3% w/w to about 3% w/w.

4. The method according to claim 3 wherein the perfumery raw material is selected from the group consisting of benzyl salicylate, benzyl benzoate, anisic aldehyde, isoeugenol methylether, cinnamyl acetate and eugenol.

5. Perfume base according to claim 1 wherein the concentration of usnic acid is about 0.5% w/w to about 2% w/w.

6. The method according to claim 3 wherein the concentration of usnic acid in said perfume composition is about 0.5% w/w to about 2% w/w.

* * * * *

UNITED STATES PATENT AND TRADEMARK OFFICE
CERTIFICATE OF CORRECTION

PATENT NO. : 5,306,706
DATED : April 26, 1994
INVENTOR(S) : Ahmet E. Baydar et al.

It is certified that error appears in the above-identified patent and that said Letters Patent is hereby corrected as shown below:

Title Page, [86], § 371 and § 102(e) dates should read December 7, 1992.

Signed and Sealed this

Twentieth Day of September, 1994

Attest:

BRUCE LEHMAN

*Attesting Officer*     *Commissioner of Patents and Trademarks*